(12) United States Patent
Chang et al.

(10) Patent No.: US 9,000,034 B2
(45) Date of Patent: Apr. 7, 2015

(54) ANTIBIOTIC COMPOSITION CONTAINING ERYTHORBYL LAURATE AND ITS USAGE

(71) Applicant: SNU R&DB Foundation, Seoul (KR)

(72) Inventors: Pahn Shick Chang, Seoul (KR); Kyung Min Park, Seoul (KR); Da Eun Lee, Seoul (KR); Dong Hyun Kang, Seoul (KR)

(73) Assignee: SNU R&DB Foundation, Seoul (KR)

( * ) Notice: Subject to any disclaimer, the term of this patent is extended or adjusted under 35 U.S.C. 154(b) by 0 days.

(21) Appl. No.: 13/780,835

(22) Filed: Feb. 28, 2013

(65) Prior Publication Data

US 2014/0113963 A1  Apr. 24, 2014

(30) Foreign Application Priority Data

Oct. 23, 2012 (KR) .................. 10-2012-0117874

(51) Int. Cl.
*A61K 31/34* (2006.01)
*A01N 43/08* (2006.01)
*A61K 31/375* (2006.01)

(52) U.S. Cl.
CPC .............. *A01N 43/08* (2013.01); *A61K 31/375* (2013.01)

(58) Field of Classification Search
None
See application file for complete search history.

(56) References Cited

PUBLICATIONS

Park et al., LAMI-085 Erythorbyl Laurate: A Promising Candidate for Novel Antimicrobial Agent with Antioxidative Activity, 10th Euro Fed Lipid Congress, Cracow, Sep. 23-26, 2012 (Abstract).*
Park et al., Lipase-catalyzed synthesis of erythorbyl laurate in acetonitrile, Food Chemistry (2011), 129(1), 59-63.*
STN document No. 155:180402.*

* cited by examiner

*Primary Examiner* — Svetlana M Ivanova
(74) *Attorney, Agent, or Firm* — Mintz Levin Cohn Ferris Glovsky and Popeo, P.C.; Kongsik Kim

(57) ABSTRACT

An antibiotic composition including erythorbyl laurate as an active ingredient and a use thereof are disclosed. Erythorbyl laurate is confirmed to have antibiotic effects on Gram-positive bacteria and thus is used as an antibiotic agent in foods, cosmetics, feeds, and the like and utilized in the form of a hand cleaner and other medicines for external application.

6 Claims, 7 Drawing Sheets

ANTIBIOTIC COMPOSITION CONTAINING ERYTHORBYL LAURATE AND ITS USAGE

CROSS-REFERENCE TO RELATED APPLICATIONS

This application claims priority to Korean Application No. Patent Application No. 2012-0117874 filed on Oct. 23, 2012, which is incorporated herein by reference.

TECHNICAL FIELD

The present invention relates to an antibiotic composition containing erythorbyl laurate as an active ingredient and a use thereof.

BACKGROUND ART

Passing through modernization and industrialization, the scale of the Korean economy increased and Korean society and industry as a whole dramatically changed. The food industry is no exception. In comparison with the past, diets have dramatically changed and Korean society is increasingly aware of food safety.

Among problems in terms of food safety, problems related to food poisoning are major social issues and emphasis on food safety is gradually increasing. Most cases of food poisoning are caused by bacteria. According to statistics of the Korea Food and Drug Administration, the number of patients with food poisoning was 5,999 in 2009 and 7,218 in 2010.

To prevent food poisoning, various kinds of antibiotic agents have been developed and are substantially used in foods. However, antibiotic agents are one of the factors that pose a significant danger to human health. Therefore, there is a need to develop safer antibiotic agents.

Korean Patent Application Publication No. 10-2006-0075800 (publication date: Jul. 4, 2006) discloses an antimicrobial composition for food which includes 20 to 50 wt % of an organic acid, 10.0 to 20.0 wt % of an organic acid salt, 0.1 to 1.0 wt % of chitosan oligosaccharide, 1.0 to 10.0 wt % of phyollen, and water constituting the remaining fraction. The invention disclosed in patent document 1 provides a novel antimicrobial composition suitable for use as an antimicrobial agent for foods and general purposes which includes an organic acid, an organic acid salt, chitosan oligosaccharide, and phyollen at a particular ratio and thus has excellent antimicrobial effects, which results in improved food preservation, has no breakdown of nutrients or no reduction in the texture of food, is not harmful to the human body, and has reduced sourness as compared to conventional acidulants.

SUMMARY OF THE INVENTION

Therefore, the present invention has been made in view of the above problems, and it is an object of the present invention to provide an antibiotic agent having high safety to the human body.

The present invention provides an antibiotic composition containing erythorbyl laurate as an active ingredient.

The inventors of the present invention synthesized erythorbyl laurate through polymerization of erythorbic acid, which is also called vitamin C and an isomer of ascorbic acid, and lauric acid, which is a fatty acid having carbon atoms and confirmed antibiosis of erythorbyl laurate.

Erythorbic acid is a stereoisomer of ascorbic acid and is also called 'D-isoascorbic acid' or 'D-araboascorbic acid.' Erythorbic acid has chemical formula $C_6H_8O_6$ and is advantageously available at relatively low cost because 2-ketogluconate is easily converted into erythorbic acid in glucose fermentation.

Lauric acid has chemical formula $CH_2(CH_2)_{10}COOH$ and is called 'dodecylic acid' or 'dodecanoic acid.' Lauric acid is chain fatty acid having 12 carbon atoms and contained in coconut oil or the like. In the human body, lauric acid is contained as heavy chain fatty acid and is metabolized in the liver through $\beta$-oxidation.

Erythorbyl laurate may be synthesized using various methods. In an embodiment, erythorbyl laurate may be synthesized from erythorbic acid and lauric acid using a lipase. The lipase may be used in an immobilized state for synthesis using an enzyme. In a reaction using an immobilized enzyme, the immobilized enzyme does not react with a substrate or product of the reaction and is involved in the synthesis of a product under enzyme reaction conditions, such as pH, temperature, and pressure. This method is advantageous in that recovery and reuse of the enzyme after the reaction is easy, the reaction is easily stopped through the recovery of the enzyme, and separation and purification of the product are easy because the enzyme is not contained in the product. In addition, enzyme stability may be improved through immobilization.

In the present invention, apoptotic effects and proliferation inhibitory effects of erythorbyl laurate on Gram-positive bacteria and Gram-negative bacteria were evaluated, and it was confirmed that erythorbyl laurate has a high apoptotic capability for Gram-positive bacteria. In addition, erythorbyl laurate was confirmed to have no cytotoxicity.

In an embodiment, the antibiotic composition may be a pharmaceutical composition, a hand cleaner composition, or an agrochemical composition.

The amount of erythorbyl laurate in the pharmaceutical composition may be adjusted according to a method of using a preventive and therapeutic agent, conditions of a user (animal), types of diseases, and severity of diseases. In the antibiotic composition, the amount of erythorbyl laurate in a pharmaceutical composition or an animal medicine composition may range from 0.000001 wt % to 50 wt %, but is not limited thereto. When the amount of erythorbyl laurate is less than 0.000001 wt %, however, prevention and treatment effects may be insignificant and, on the other hand, when the amount of erythorbyl laurate is greater than 50 wt %, an increase rate in effects with respect to the amount used may be low and thus use of erythorbyl laurate in this amount may be uneconomical. The concentration of erythorbyl laurate in the pharmaceutical composition or the animal medicine composition may be 10 $\mu$M to 1 mM, but is not limited thereto.

The pharmaceutical composition or animal medicine composition may further include a pharmaceutically acceptable carrier, a diluent, or an excipient, in addition to the active ingredient. The pharmaceutically acceptable carrier, the excipient, or the diluent may be at least one of lactose, dextrose, sucrose, sorbitol, mannitol, xylitol, erythritol, maltitol, starch, gum acacia, alginates, gelatin, calcium phosphate, calcium silicate, cellulose, methyl cellulose, microcrystalline cellulose, polyvinylpyrrolidone, water, methylhydroxy benzoate, propylhydroxy benzoate, talc, magnesium stearate, and mineral oil. In addition, when a preventive and therapeutic agent is a medicine, the antibiotic composition may further include a filler, an anticoagulant, a lubricant, a wetting agent, a flavor enhancer, an emulsifying agent, a preservative, or the like.

Formulation of the pharmaceutical composition or the animal medicine composition may be adjusted according to application. In particular, the pharmaceutical composition or the animal medicine composition may be formulated using a method known in the art so as to provide rapid, continuous or delayed release of the active ingredient after administration to mammals. For example, the formulation may be any one selected from among plasters, granules, lotions, liniments, lemonades, aromatic waters, powders, syrups, ophthalmic ointments, liquids and solutions, aerosols, extracts, elixirs, ointments, fluidextracts, emulsions, suspensions, decoctions, infusions, ophthalmic solutions, tablets, suppositories, injections, spirits, cataplasm, capsules, creams, troches, tinctures, pastes, pills, and soft or hard gelatin capsules.

A suitable dose of the pharmaceutical composition or the animal medicine composition may be determined considering administration methods, ages of users (e.g., animals), gender and body weight, disease severity, and the like. In an embodiment, a preventive and therapeutic agent according to the present invention may be administered at least once in an amount of 0.1 to 100 mg/kg (body weight) per day based on the amount of the active ingredient. However, the dose of the pharmaceutical composition or the animal medicine composition is not limited to the above-described example, and may be adjusted by a doctor according to conditions of users (animals).

The hand cleaner composition may be prepared by adding erythorbyl laurate to a general hand cleaner base. The hand cleaner base may include a gelling agent, distilled water, or the like and further include a curing accelerator, a skin moisturizer, and nutritional supplements.

The agrochemical composition may be prepared through addition of an agriculturally effective amount of erythorbyl laurate and be used as a germicide.

The present invention also provides a food composition containing erythorbyl laurate as an antibiotic agent. The food composition may be any one selected from among meats, cereals, caffeinated beverages, general drinks, chocolates, breads, snacks, confectionery, pizza, jelly, noodles, gums, ice creams, alcoholic beverages, liquors, vitamin compounds, and other health food supplements, but is not limited thereto. The amount of erythorbyl laurate in the food composition may be a general amount added as an antibiotic agent or a preservative.

The present invention also provides a cosmetic composition including erythorbyl laurate as an antibiotic agent. Formulation of the cosmetic composition is not particularly limited and includes any formulation that may be used as cosmetics. The formulation of the cosmetic composition may be a basic cosmetic formulation in the form of facial lotions, gels, water-soluble liquids, creams, or essence lotions, or of an oil-in-water type or a water-in-oil type, oil-in-water or water-in-oil type makeup base, foundation, skin cover, lipsticks, face powder, two-way cake, or colored cosmetic formulations including eye shadow, cheek colors, and eyebrow pencils. The amount of erythorbyl laurate in cosmetics may be a general amount added as an antibiotic agent or a preservative.

The present invention also provides a feed composition or a feed additive composition that includes erythorbyl laurate as an antibiotic agent. The feed composition or the feed additive composition may be prepared through addition of erythorbyl laurate as an antibiotic agent, and formulation thereof is not particularly limited.

The present invention also provides a method of sterilizing bacteria using erythorbyl laurate as an antibiotic agent. The method is characterized in that erythorbyl laurate is used as a sterilizing ingredient. For example, the method may entail sprinkling onto germ-contaminated crops or sites, e.g., spraying or the like, or may be performed using toilet paper, a towel, or a dish towel soaked with erythorbyl laurate.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION

Hereinafter, the present invention will be described more fully with reference to the following Examples and Experimental Examples, and these examples are for illustrative purposes only and are not intended to limit the scope of the invention. In addition, the present invention includes all modifications and equivalents of the technical subject matters of the invention.

Example 1

Synthesis of Erythorbyl Laurate

An immobilized lipase derived from *Candida Antarctica* and having a catalytic activity of 7000 PLU/g, i.e., triacylglycerol hydrolase, EC 3.1.1.3; Novozym 435, was used in synthesis of erythorbyl laurate.

Erythorbic acid (≥99.0%, Fluka, Sigma-Aldrich) and lauric acid (≥99.0%, Fluka, Sigma-Aldirch) were prepared as raw materials for the synthesis of erythorbyl laurate, and acetonitrile (J. T. Baker Co., Philips burg, NJ USA) was used.

In addition, high performance liquid chromatography (HPLC) (LC-2002, Jasco, Tokyo, Japan) was used to confirm a product after synthesis, and HPLC was performed using a 0.45 μm membrane filter, HPLC grade acetonitrile, a refractive index detector RI-2031 (manufactured by Jasco), and an ultraviolet detector UV-2075 (manufactured by Jasco).

Figure 1:
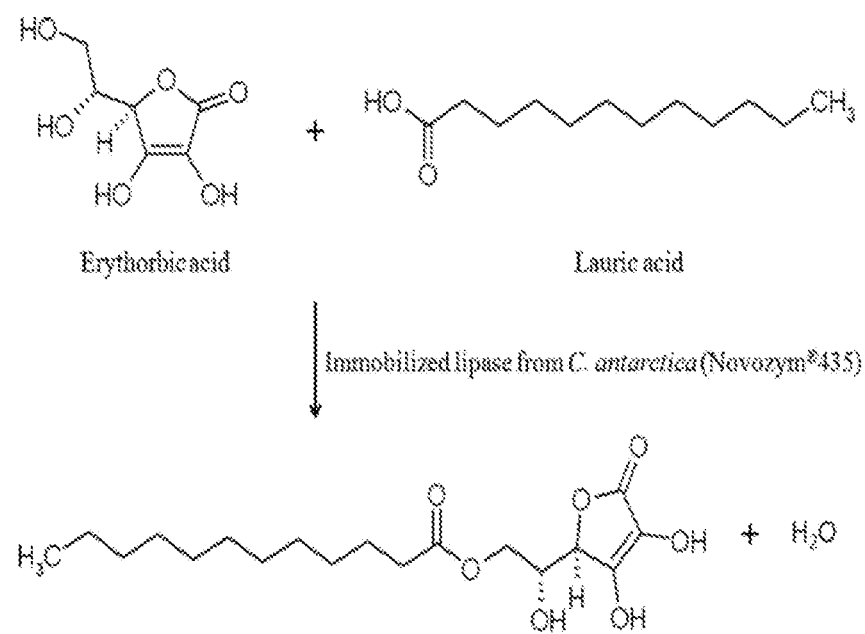
FIG. 1 illustrates a process of synthesizing erythorbyl laurate using an immobilized lipase.

To synthesis erythorbyl laurate, 0.12 mmol of erythorbic acid and 0.60 mmol of lauric acid were added to a vial along with 20 ml of acetonitrile. The resulting solution was stirred at 200 rpm and 50° C. for 30 minutes in an optical shaking water bath. After stirring, 200 mg of an immobilized lipase was added to the resulting solution to induce a reaction therebetween. During the reaction, a temperature was maintained at 50±1° C. FIG. 1 illustrates a process of synthesizing erythorbyl laurate using an immobilized lipase.

Meanwhile, to observe esterification of erythorbic acid and lauric acid over time (degree of formation of erythorbyl laurate), a sample was collected at predetermined time intervals and analyzed by HPLC.

For HPLC analysis, the reaction mixture was collected at appropriate time intervals and filtered through a membrane filter. 20 µl of the filtrate was each injected into HPLC. Acetonitrile/water/acetic acid (90:5:5. v/v/v) was used as a mobile phase, and a flow rate of 1.0 ml/min was maintained for 15 minutes. A degree of esterification was obtained using Equation 1 below.

Degree of esterification(%)={erythorbyl laurate/(erythorbic acid+erythorbyl laurate)}*100     <Equation 1>

Figure 2:
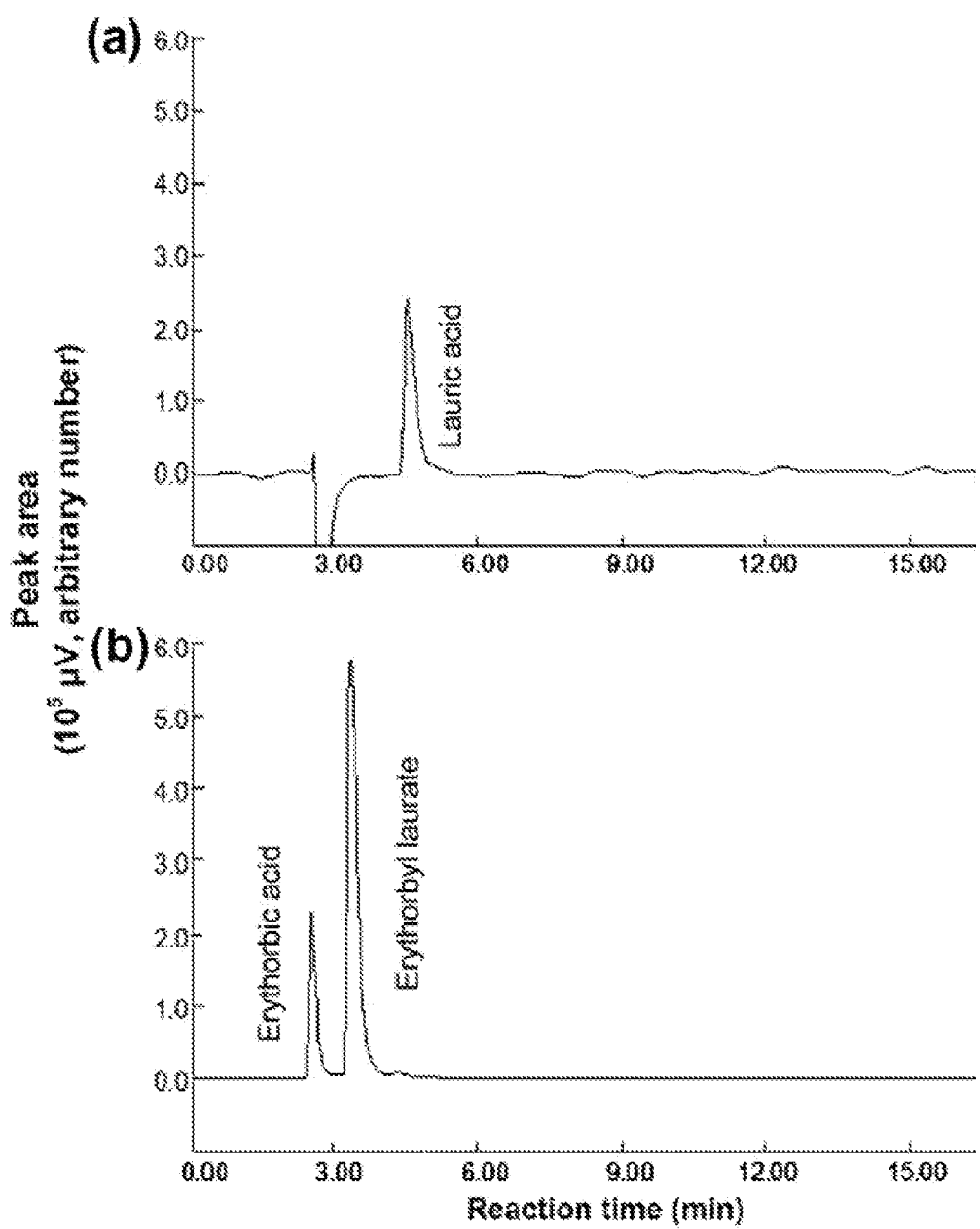
FIG. 2 illustrates graphs showing high performance liquid chromatography (HPLC) chromatograms of synthesis products of erythorbic acid and lauric acid using an immobilized lipase (FIG. 2(a): RI-detector and FIG. 2(b): UV-detector)

As a result of analysis, as illustrated in FIG. 2, retention times of erythorbic acid, erythorbyl laurate, and lauric acid were 2.506±0.014, 3.386±0.027, and 4.628±0.032 min, respectively.

Figure 3:
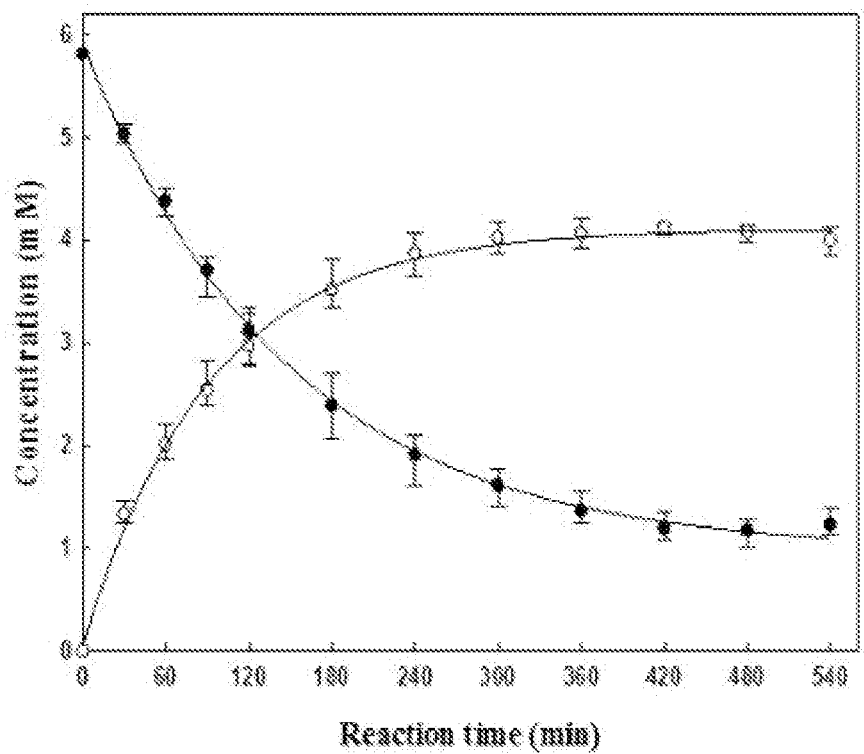
FIG. 3 is a graph showing change in concentration according to reaction time of erythorbic acid and lauric acid using an immobilized lipase (•: erythorbic acid and ○: erythorbyl laurate)

As illustrated in FIG. 3, as the reaction proceeds, the concentration of erythorbic acid decrease, while the amount of erythorbyl laurate produced gradually increases. 8 hours after reaction initiation, the degree of esterification reaches a maximum value (approximately 78.5) and does not proceed further. This is because the esterification reached equilibrium.

Synthesis of erythorbyl laurate through HPLC was confirmed, and the degree of esterification over time was evaluated.

Example 2

Antibiosis Test of Erythorbyl Laurate (1) Test for Apoptotic Effects

Apoptotic effects of erythorbic acid, lauric acid, and erythorbyl laurate, which is a polymerized product of erythorbic acid and lauric acid and a material of interest in this experiment, on two kinds of Gram-negative bacteria and two kinds of Gram-positive bacteria were evaluated.

As selective media for antibiosis test, sorbitol MacConkey agar (SMAC) (available from Difco), Xylose Lysine Desoxycholate agar (XLD) (available from Difco), Oxford agar base with Bacto™ Oxford antimicrobial supplement (MOX) (available from Difco), and Baird-Parker Agar Base (BPA) (available from Difco) were used.

As bacterial strains, $Escherichia\ coli$ O157:H7 (ATCC 35150), $Salmonella\ typhimurium$ (ATCC 19586), $Listeria\ monocytogenes$ (ATCC 19114), and $Staphylococcus\ aureus$ (ATCC 27213) were prepared. Each of the bacterial strains was cultured in tryptic soy broth (Difco, Becton Dickinson, Sparks, Md., USA) for 24 hours at 37° C., centrifuged at 4000×g for 20 minutes at 4° C., and purified with buffered peptone water (BPW) (available from Difco). Each strain was prepared in the form of a bacterial suspension ($10^6$ CFU/ml).

For this experiment, first, 10 ml of erythorbic acid, 10 ml of lauric acid, and 10 ml of erythorbyl laurate were added to 0.1 ml of each bacterial suspension. The resulting solution was satisfactorily mixed using a vortex mixer for minutes. Thereafter, 1 ml of the resultant solution obtained by mixing each bacterial suspension and test compounds was mixed with 9 ml of sterilized peptone water. Then, the resulting mixture was diluted 1:10 using sterilized peptone water. 0.1 ml of the diluted solution was collected and plated on the selective media. The plated media were incubated at 37° C. for 24 hours, and then colonies grown in each plate were measured in $\log_{10}$ CFU/ml.

Figure 4:
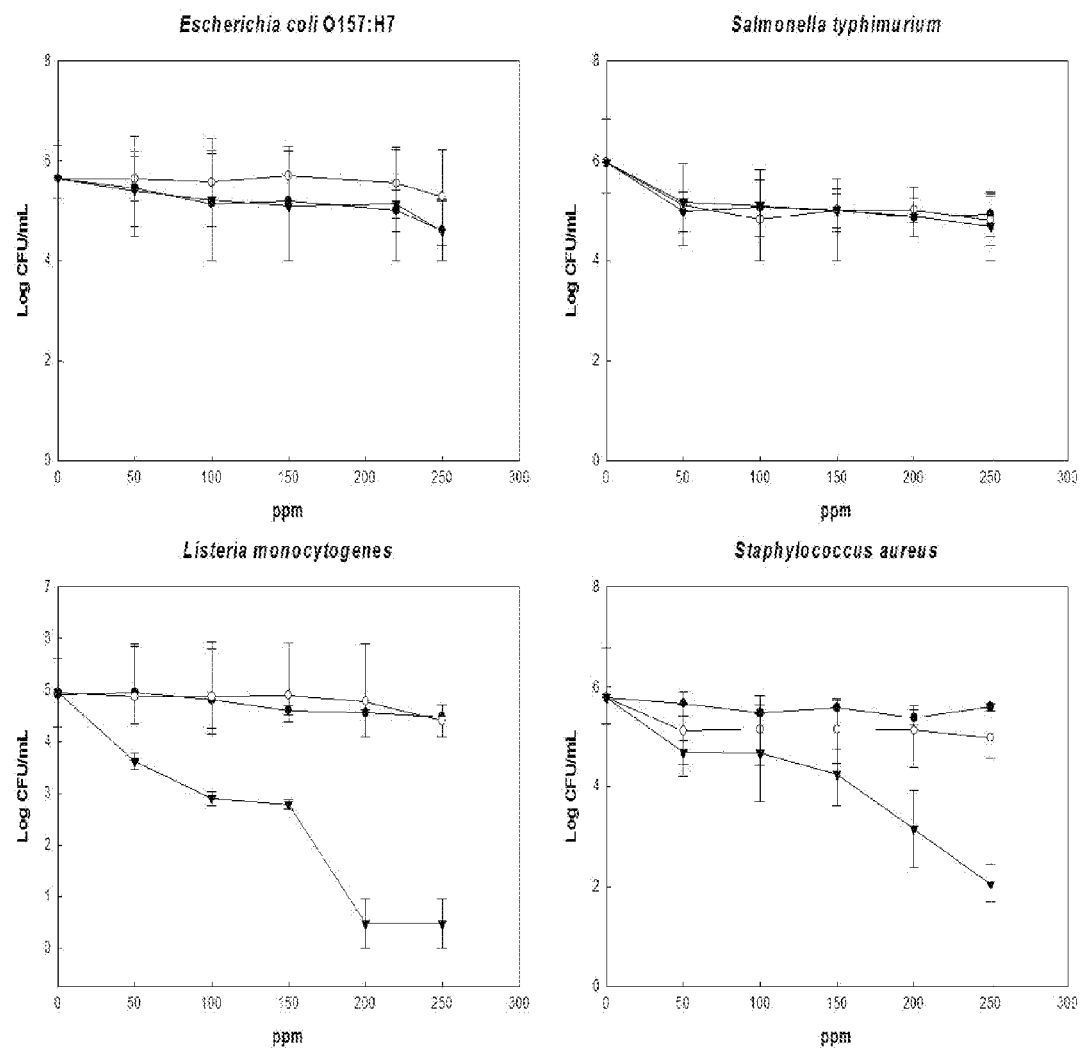
FIG. 4 illustrates graphs showing apoptotic effects of erythorbic acid, lauric acid, and erythorbyl laurate (•: erythorbic acid, ○: lauric acid, and ▼: erythorbyl laurate)

As a result of the experiment (see FIG. 4), apoptotic effects of erythorbyl laurate on Gram-negative bacteria, i.e., $Escherichia\ coli$ O157:H7 (ATCC 35150) and $Salmonella\ typhimurium$ (ATCC 19586) were insignificant as compared with those of erythorbic acid and lauric acid on the Gram-negative bacteria. By contrast, erythorbyl laurate exhibited excellent apoptotic effects on Gram-positive bacteria, i.e., $Listeria\ monocytogenes$ and $Staphylococcus\ aureus$.

Decrease in the number of Gram-positive bacteria according to the concentration of erythorbyl laurate was evaluated. Erythorbyl laurate exhibited gradually increased apoptotic effects on $Listeria\ monocytogenes$ exhibiting decrease in viable cell count as the concentration of erythorbyl laurate was increased. It was confirmed that the viable cell count was constantly decreased up to 200 ppm. That is, the apoptotic effects were increased in proportion to increase in the concentration of erythorbyl laurate, while viable cell count was maintained at 0.48 CFU/ml above concentrations of 200 ppm.

As for $Staphylococcus\ aureus$, decrease in viable cell count became bigger as the concentration of erythorbyl laurate increased, as in the case of $Listeria\ monocytogenes$. However, the case of $Staphylococcus\ aureus$ was different from the case of $Listeria\ monocytogenes$ in that erythorbyl laurate exhibited continuous apoptotic effects even at a concentration of 200 ppm or higher.

(2) Test for Bacterial Proliferation Inhibitory Effects

Apoptotic effects on two kinds of Gram-positive bacteria and two kinds of Gram-negative bacteria were examined, and then erythorbyl laurate was expected to have not only apoptotic effects on bacteria and but also bacterial proliferation inhibitory effects. An experiment to verify these effects was performed as follows.

To evaluate the bacterial proliferation inhibitory effects of erythorbyl laurate, a 96-well microtiter panel, Mueller Hinton Broth (MHB) (available from Difco), a microtiter plate SpectaMax M2 (Molecular Devices, USA), and the same bacteria as those used in the test to verify the apoptotic effects were prepared.

First, 100 µl of each of the samples was inoculated with 100 µl of a bacterial strain solution containing $10^5$ CFU/ml of test bacterial strains. Each sample was incubated at 37° C. for 22 hours with absorbance of each sample being measured at 600 nm using a microtiter plate at intervals of 20 minutes.

Figure 5:
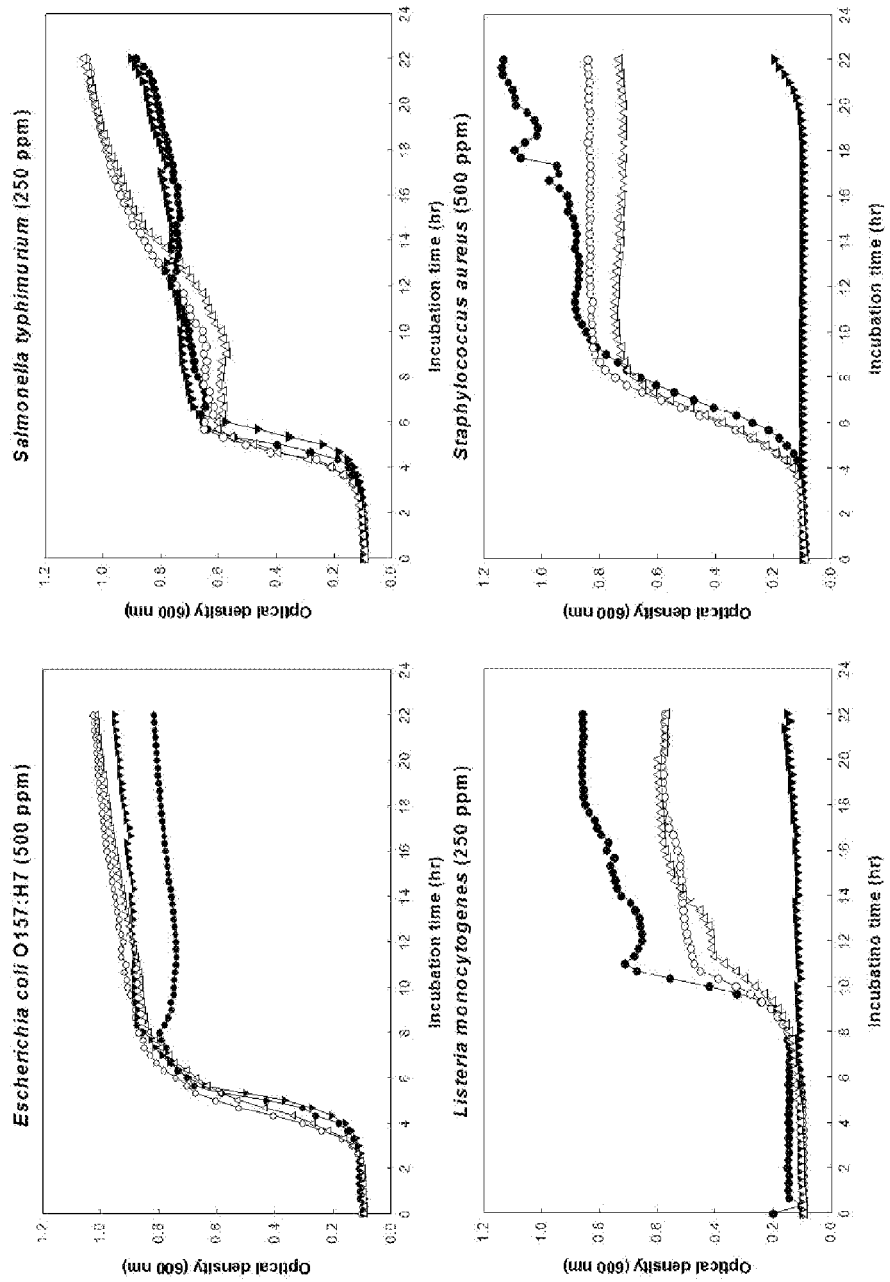
FIG. 5 illustrates graphs showing bacterial growth inhibitory effects of erythorbic acid, lauric acid, and erythorbyl laurate (•: erythorbic acid, Δ: lauric acid, ▼: erythorbyl laurate, and ○: control)

As result of the experiment (see FIG. 5), aspects of the test results similar to the test results for apoptotic effects were obtained. All the erythorbic acid, lauric acid, and erythorbyl laurate had insignificant bacterial proliferation inhibitory effects on Gram-negative bacteria, i.e., $Escherichia\ coli$ O157:H7 (ATCC 35150) and $Salmonella\ Typhimurium$ (ATCC 19586). By contrast, erythorbyl laurate had effective bacterial proliferation inhibitory effects on Gram-positive bacteria, i.e., $Listeria\ monocytogenes$ and $Staphylococcus\ aureus$. The bacterial proliferation inhibitory effects on the Gram-positive bacteria lasted for 20 to 22 hours.

Figure 6:
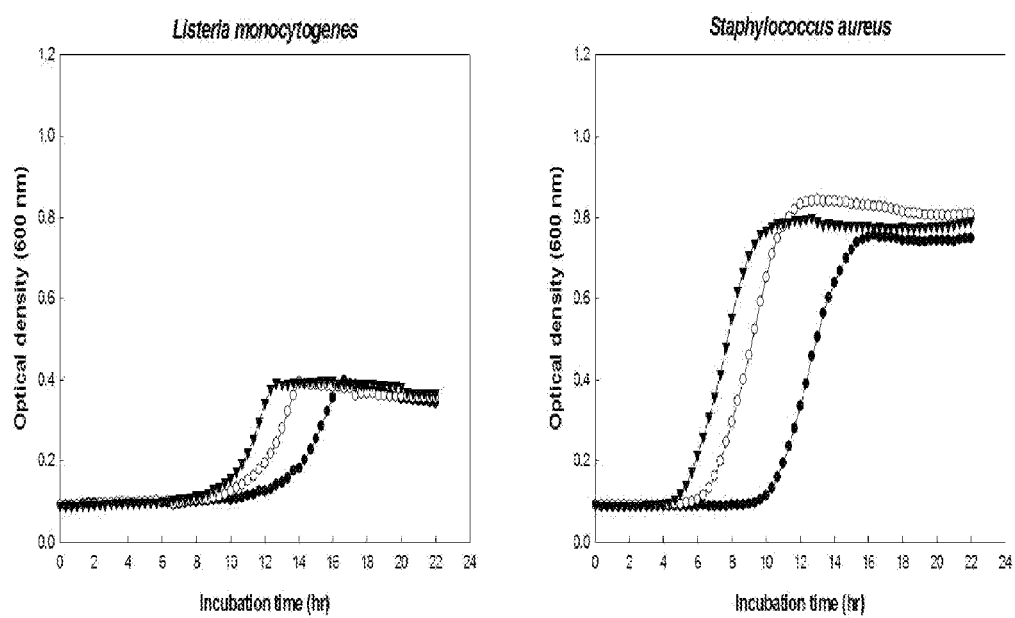
FIG. 6 illustrates graphs showing growth inhibitory effects of each bacterium according to the concentration of erythorbyl laurate.

Meanwhile, as a result of examination of proliferation inhibition data of $Staphylococcus\ aureus$, a portion where an exponential phase of the bacteria starts was remarkably shown unlike $Listeria\ monocytogenes$. Thus, the concentration of erythorbyl laurate was further decreased and a growth curve of the bacteria was measured. As a result of comparison under the same conditions, as the concentration of erythorbyl laurate added decreased, an induction phase decreased and the exponential phase was observed earlier (see FIG. 6).

Experimental Example 1

Cytotoxicity Test of Erythorbyl Laurate

To confirm safety of erythorbyl laurate as a food additive, cell viability was evaluated by performing 3-(4,5-dimethylthiazolyl)-2,5-diphenyl tetrazolium bromide (MTT) assay. A test for cytotoxicity of erythorbyl laurate on human intestinal epithelial cells INT-407 was performed in comparison with ascorbic acid, erythorbic acid, and ascorbyl palmitate, which are used as food additives.

For this experiment, MTT (available from Sigma), human intestinal epithelial cells INT-407 (ATCC CCL-6), ascorbyl palmitate, erythorbyl laurate, erythorbic acid, lauric acid, DMSO (available from Sigma), fetal bovine serum (GIBCO-BRL, Gaithersburg, Md., U.S.A.), cell culture medium MEM (minimum essential medium), a 96-well culture plate (SPL Life Sciences), and an incubator were prepared.

First, ascorbyl palmitate and erythorbyl laurate were dissolved in DMSO and diluted in MEM with 10% (v/v) fetal bovine serum (FBS).

The INT-407 cells were cultured in a humidified incubator containing 5% $CO_2$ at 37° C. together with various concentrations of ascorbyl palmitate, erythorbyl laurate, erythorbic acid, and lauric acid after the number of the INT-407 cells put into each well of the 96-well culture plate was adjusted to $1 \times 10^5$. After culturing, MTT was added to a final concentration of 0.5 mg/ml to each well, and the INT-407 cells were incubated in a dark room for 4 hours using a predetermined method. To dissolve formazan crystal, 200 µl of an MTT solubilization solution (10% triton X-100 in isopropanol containing 0.1 N HCl) was added to each well and completely mixed. Absorbance of the 96-well culture plate containing the INT-407 cells was measured based on optical density (OD) at a wavelength of 570 nm ($OD_{570}$), and basic absorbance of the 96-well culture plate was measured based on $OD_{600}$. Here, cell viability was defined by a difference between the measured $OD_{570}$ value and the measured $OD_{690}$ value.

Figure 7:
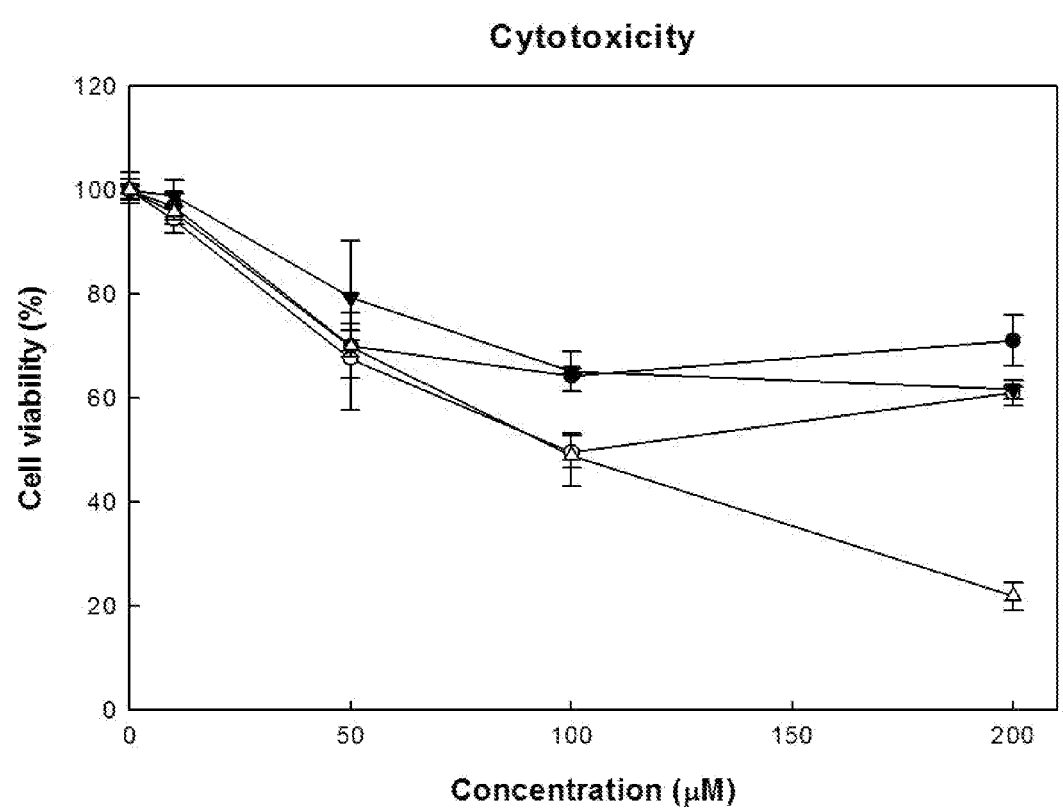
FIG. 7 is a graph showing cytotoxicity test results of erythorbyl laurate (•: erythorbic acid, ○: lauric acid, ▼: erythorbic laurate, and Δ: ascorbyl palmitate).

As a result of the experiment (see FIG. 7), when the INT-407 cells were inoculated with erythorbyl laurate, the INT-407 cells exhibited a higher cell viability at all the concentrations of erythorbyl laurate than a case when ascorbyl palmitate currently used as a food additive was used, and exhibited cell viability similar to that when erythorbic acid was used, at concentrations of erythorbyl laurate, i.e., 50 µM and 200 µM.

Preparation Example 1

Preparation of Pharmaceutical Composition

An antibiotic pharmaceutical composition was prepared as follows.

(1) Preparation of Powder 2 g of erythorbyl laurate and 1 g of lactose were mixed and filled in an airtight pack to prepare a powder formulation.

(2) Preparation of Tablet 100 mg of erythorbyl laurate, 100 mg of cornstarch, 100 mg of lactose, and 2 mg of magnesium stearate were mixed and compressed into a tablet according to a conventional tablet preparation method to prepare a table formulation.

(3) Preparation of Capsule 100 mg of erythorbyl laurate, 100 mg of cornstarch, 100 mg of lactose, and 2 mg of magnesium stearate were mixed and a gelatin capsule was filled with the mixture to prepare a capsule formulation.

(4) Preparation of Injectable Liquid Formulation

An appropriate amount of distilled water for injection was added to 100 mg of erythorbyl laurate and erythorbyl laurate was dissolved therein, the resulting solution was adjusted to a pH of about 7.5 and filled into a 2 mL ampoule and sterilized, thereby completing preparation of an injectable solution.

Preparation Example 2

Preparation of Food Composition

A sausage food composition containing erythorbyl laurate was prepared as follows: 65.18 wt % of pork, 25 wt % of chicken, 3.5 wt % of starch, 1.7 wt % of soybean protein, 1.62 wt % of salt, 1.4 wt % of glucose, 1.5 wt % of glycerin, and 0.1 wt % of erythorbyl laurate were mixed together and sausage was prepared using the resulting mixture using a conventional method.

Preparation Example 3

Preparation of Hand Cleaner 67.67 g of ethanol, 0.05 g of rose fragrance, 24.33 g of distilled water, 0.5 g of glycerin, and 0.047 g of erythorbyl laurate were added to a beaker, and the resulting solution was stirred at 3,000 rpm at 25° C. for 1 minute. To the stirred solution was sequentially added 0.5 g of propylene glycol, 1.5 g of isopropyl alcohol, 0.5 g of isopropyl myristate, 0.004 g of oligosaccharide, and 0.004 g of chitosan, and the resulting mixture was stirred using a stirrer for about 1 minute. While stirring, 0.2 g of diisopropanolamine was added thereto. Subsequent processes were performed using a known method, thereby completing preparation of a hand cleaner.

Preparation Example 4

Preparation of Skin Lotion 0.05 g of polypyrrolidone, 0.1 g of oleylalcohol, 0.2 g of polyoxyethylene monooleate, 0.2 g of flavoring, 0.1 g of p-hydroxybenzoate, a small amount of an antioxidant, and a small amount of pigment were mixed and dissolved in 8 g of 95% ethanol. Subsequently, 0.05 g of erythorbyl laurate and 5 g of glycerin were dissolved in 85.33 g of purified water, the above-prepared mixed solution was added thereto, and the resulting solution was stirred, thereby completing preparation of skin lotion.

Preparation Example 5

Preparation of Feed 1.0 wt % of erythorbyl laurate was added to a basic feed containing 58 wt % of fish meal, 4 wt % of soybean cake, 3 wt % of corn gluten meal, 28.7 wt % of flour, 4 wt % of squid liver oil, 1.2 wt % of vitamin complex, and 1 wt % of mineral complex to prepare 1 kg of a feed composition for flatfish farming.

As is apparent from the above description, erythorbyl laurate is confirmed to have antibiotic effects on Gram-positive bacteria and thus may be used as an antibiotic agent in foods, cosmetics, feeds, and the like and utilized in the form of a hand cleaner and other medicines for external application.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An antibiotic composition comprising erythorbyl laurate as an active ingredient.
2. The antibiotic composition according to claim 1, wherein the antibiotic composition is a pharmaceutical composition, a hand cleaner composition, or an agrochemical composition.
3. A food composition comprising erythorbyl laurate as an antibiotic agent.
4. A cosmetic composition comprising erythorbyl laurate as an antibiotic agent.
5. A feed composition comprising erythorbyl laurate as an antibiotic agent.
6. A method of sterilization using erythorbyl laurate as an antibiotic agent.

* * * * *